United States Patent [19]

Birkett et al.

[11] Patent Number: 5,302,527
[45] Date of Patent: Apr. 12, 1994

[54] NITRATE REDUCTASE AS MARKER FOR FILAMENTOUS FUNGI

[75] Inventors: John A. Birkett, Ulverston; James R. Kinghorn, St. Andrews, both of Great Britain

[73] Assignee: Glaxo Group Limited, London, England

[21] Appl. No.: 613,493

[22] PCT Filed: Mar. 2, 1990

[86] PCT No.: PCT/EP90/00372

§ 371 Date: Nov. 9, 1990

§ 102(e) Date: Nov. 9, 1990

[87] PCT Pub. No.: WO90/10074

PCT Pub. Date: Sep. 7, 1990

[30] Foreign Application Priority Data

Mar. 2, 1989 [GB] United Kingdom ............... 8904762

[51] Int. Cl.$^5$ ..................... C12N 1/15; C12N 15/80; C12P 21/00
[52] U.S. Cl. .................. 435/254.5; 435/69.1; 435/172.3; 435/320.1; 435/254.11
[58] Field of Search ............ 435/69.1, 71.1, 91, 435/172.1, 172.3, 254, 320.1, 911, 913, 933, 43, 147; 536/227; 935/6, 9, 22, 24, 27, 52, 55, 56, 59, 60, 61, 66, 68

[56] References Cited

FOREIGN PATENT DOCUMENTS

| | | |
|---|---|---|
| 0215539 | 3/1987 | European Pat. Off. ...... C12N 15/00 |
| 0227909 | 7/1987 | European Pat. Off. ...... C12N 15/00 |
| 0233715 | 8/1987 | European Pat. Off. ...... C12N 15/00 |
| 0235951 | 9/1987 | European Pat. Off. ...... C12N 15/00 |

OTHER PUBLICATIONS

Arst et al., 1979, Mol–Gen. Genet., 174:89–100.
Fu et al., 1987, PNAS, 84:8243–8247.
Timberlake et al., *Science*, 244, 1313–1317, 1989.
Unkles et al., *Molecular and General Genetics*, 99, 99–104, 1989.
Daboussi et al., *Current Genetics*, 15, 453–456, 1989.
Batt et al., *Canadian Journal of Microbiology*, 28, 1206–1209, 1982.
Unkles, *Molecular and Genetic Aspects of Nitrate Assimilation*, chapter 22, (1989 Symposium Report), Ed. J. L. Ray, J. R. Kinghorn, Oxford University Press.

*Primary Examiner*—Richard A. Schwartz
*Assistant Examiner*—Nancy T. Vogel
*Attorney, Agent, or Firm*—Bacon & Thomas

[57] ABSTRACT

The invention relates to use of the nitrate reductase gene as a selection marker in transformations of the antibiotic-producing species *Penicillium chrysogenum* and *Acremonium chrysogenum*. In particular it relates to a process for obtaining cells of *Penicillium chrysogenum* or *Acremonium chrysogenum* capable of expressing nitrate reductase from cells of the same species which are initially deficient in expression of the nitrate reductase gene (niaD-cells), which comprises introducing into said niaD-cells vector DNA including a marker gene coding for nitrate reductase operatively linked to a control sequence for expression of said gene within the selected host cells, followed by selection of cells thus transformed by their ability to grow on a suitable medium containing nitrate as the only source of nitrogen and to vector DNA for use in such a process.

6 Claims, 2 Drawing Sheets

NITRATE REDUCTASE AS MARKER FOR FILAMENTOUS FUNGI

The present invention relates to the novel use of a marker system in the transformation of filamentous fungi. In particular it relates to the use of the nitrate reductase gene as a selection marker in transformations of the antibiotic-producing species *Penicillium chrysogenum* and *Acremonium chrysogenum*.

The development and exploitation of recombinant DNA technology in filamentous fungi has been slow, in part because of the lack of efficient and industrially usable systems for readily selecting those cells which have been transformed with the desired vector DNA. Transformation and hence stable inclusion of the desired DNA into the DNA sequence of the fungal cell is a rare event and thus such a selection system for determining those few cells, perhaps among millions of untransformed cells, which have acquired the desired DNA is a necessity. Various systems have been proposed using the presence of a marker gene in the vector along with the desired DNA, by which the transformed cells can be recognised and selected.

Thus selection of successfully transformed cells of filamentous fungi has previously been demonstrated with, for example, the acetamidase (amdS) gene which confers upon transformants the ability to utilise acetamide as the sole source of nitrogen [see for instance Kelly & Hynes, EMBO J, 4, p475 (1985)] and hence provides a method of identifying such transformants. A characteristic of filamentous fungal transformation is a low efficiency of transformation, since exogenous DNA is not readily and stably integrated into the host genome. This results in a high background level of non-transformants and, in the case of the amdS selection marker system, it has been found that some of these non-transformants will also grow on acetamide as the sole nitrogen source, even though they are deficient in the expression of the acetamidase gene. This makes the amdS marker selection system difficult to operate, particularly where there is a low efficiency of transformation, since it does not clearly distinguish those cells which have undergone transformation.

This problem has been to some extent overcome by the development of antibiotic selection as a marker method. For example, transformation with a vector which includes a phosphotransferase gene as a marker confers upon the transformants resistance to the aminoglycosidic antibiotics G418 and hygromycin B [see for instance Punt et al, Gene, 56, p117 (1987)]. Transformed cells may then be recognised by their ability to grow on a medium containing one or other of these antibiotics. Although this system provides a clear-cut method of selecting transformants, the use of the resultant antibiotic resistant fungal strains on a large industrial scale is undesirable since it requires a high degree of containment making industrial exploitation both difficult and expensive. Furthermore, it is considered desirable in the use of such strains to maintain a selection pressure by the presence of antibiotic in the fermentation medium, in order to prevent growth of revertants where the integrated genes are not stably maintained; such continuous use of antibiotic in the fermentation medium is, of course, disadvantageous.

Other marker systems for filamentous fungi have been described, such as the reversions of arginine auxotrophy using the argB gene [Buxton et al, Gene, 37, p207 (1985)], tryptophan C auxotrophy using the trpC gene [Sanchez et al, Gene 51, p97 (1987)] or uracil auxotrophy using the pyr-4 or pyrG genes [Cantoral et al, Biotechnology, 5, p494 (1987)]. These techniques, however, require complicated and lengthy procedures involving mutation and selection to obtain suitable auxotrophic mutants. Also such procedures often lead to a loss of antibiotic productivity in antibiotic producing strains of filamentous fungi.

There is a need, therefore, to develop a marker system for the identification of transformed filamentous fungi where isolation of suitable mutants which are deficient in the expression of the marker gene is straightforward and selection procedures provide clear and ready identification of the transformed cells without the use of antibiotic resistance markers. Furthermore, such a system will ideally involve the use of a homologous gene as the marker gene (i.e. a gene from the same species as that being transformed); in the case of a homologous gene as the marker gene, expression and transformation frequency are likely to be optimised since the genetic code will be native to the transformed host and hence more readily recognised by the host cell, leading to more efficient expression of the gene. Also, it is preferable to avoid introduction of foreign genes into a host filamentous fungus so as to reduce any environmental risks.

We have now found that transformed cells of the antibiotic producing filamentous fungi *Penicillium chrysogenum* and *Acremonium chrysogenum* may be successfully and efficiently selected by the use of a nitrate reductase marker gene in the transformation of cells deficient in nitrate reductase. Such a system provides clear-cut selection of transformants, avoids the disadvantages of the insertion of antibiotic resistance and allows, if desired, the use of a homologous gene as the marker gene.

Thus in one aspect of the present invention, we provide a process for obtaining cells of *Penicillium chrysogenum* or *Acremonium chrysogenum* capable of expressing nitrate reductase from cells of the same species which are initially deficient in expression of the nitrate reductase gene (niaD$^-$ cells), which comprises introducing into said nia D$^-$ cells vector DNA including a marker gene coding for nitrate reductase operatively linked to a control sequence for expression of said gene within the selected host cells, followed by selection of cells thus transformed by their ability of grow on a suitable medium containing nitrate as the only source of nitrogen.

Strains of *Penicillium chrysogenum* and *Acremonium chrysogenum* (formerly know as *Cephalosporium acremonium*) which ma be used in the process of the invention are preferably antibiotic producing strains or nitrate reductase deficient mutants thereof. Strains of *P. chrysogenum* are widely used in the industrial production of penicillin antibiotics such as penicillin G and penicillin V. Similarly, strains of *A. chrysogenum* are used in the production of cephalosporin antibiotics such as cephalosporin C, deacetylcephalosporin C and deacetoxycephalosporin C.

The biosynthesis of both penicillins and cephalosporins begins with the condensation of three amino acids, L-α-aminoadipic acid, L-cysteine and L-valine by the enzyme ACV synthetase. The tripeptide which is formed is cyclised by the enzyme isopenicillin N systhetase to produce isopenicillin N. In *P. chrysogenum* isopenicillin N is converted to a number of derivatives of 6-aminopenicillanic acid including, for example, the phenylacetic acid derivative, penicillin G, and the phenoxyacetic acid derivative, penicillin V. In *A. chrysogenum* isopenicillin N undergoes modification by the enzyme deacetoxycephalosporin C synthetase (also known as expandase) which converts the thiazolidine ring of the penam structure into the dihydrothiazine ring of the cephem structure, to give deacetoxycephalosporin C. This is converted by the enzyme deacetylcephalosporin C synthetase (also known as hydroxylase) to deacetylcephalosporin C. (In *A. chrysogenum* the expandase and hydroxylase enzyme activities are located on the same protein molecule). The deacetylcephalosporin C is then acetylated by the enzyme DAC acetyltransferase to cephalosporin C.

The vector DNA which is integrated into the fungal genome in the process of the invention preferably includes, as well as the marker gene coding for nitrate reductase, at least one industrially important gene which will result in an improved strain following transformation. Thus the gene to be introduced may be, for example, one which will improve the productivity or cost effectiveness of antibiotic fermentation and hence may be, for instance, a gene involved in the biosynthetic pathway of penicillins or cephalosporins, a regulatory gene involved in the productive phase of growth of the organism, a gene which allows growth of the organism on a novel substrate or a gene which will change the metabolite produced. Genes which may be inserted include a gene coding for the enzymes ACV synthetase, isopenicillin N synthetase, deacetoxycephalosporin C synthetase or DAC acetyltransferase. For the reasons discussed above, these genes are preferably isolated from the same species as that being transformed.

In an alternative procedure according to the process of the invention, the gene which it is desired to insert into the fungal genome and the nitrate reductase marker gene may be located on different vectors, since there is considerable likelihood that is host strain transformed by the vector containing the selectable marker will also have been transformed by the desired gene, even when they are located on separate vectors.

The transformed strain prepared by the procedure of the invention will possess either a new gene or multiple copies of one of its existing genes such as a biosynthesis pathway gene and will thus have operational advantages for the production of penicillins or cephalosporins compared with the parental strain. Examples of such advantages include improved growth rate or titre of the penicillin or cephalosporin; improved stability; improved growth characteristics on different media; and improved ease of extraction of the products.

The desired genes which are integrated into the fungal genome according to the process of the invention may be prepared by conventional techniques known in the art, or using a method analogous to that described herein for the nitrate reductase gene.

Suitable host cells of *P. chrysogenum* and *A. chrysogenum* to be transformed by the process of the invention are strains deficient in the expression of the nitrate reductase structural gene (niaD). They are therefore unable to utilise nitrate as a source of nitrogen and hence are unable to grow on a minimal medium where nitrate is the sole nitrogen source. Such deficient strains are thus readily distinguished from strains transformed by the process of the invention which have a nitrate reductase gene as a selectable marker.

Nitrate reductase deficient strains may arise with low frequency by spontaneous mutation. Alternatively, mutation may be induced by standard mutagenesis techniques. Such techniques include chemical mutagenesis working at the DNA level, for example, 5-bromouracil and 2-aminopurine may be incorporated into the DNA sequence during DNA replication in place of thymidine and adenine, respectively, causing miscopying errors. Chemical modification of nucleotides may alter pairing in the DNA, for example, nitrous acid may deaminate adenine, cytosine and guanine, and hydroxylamine specifically attacks cytosine (to form N-6-hydroxycytidine) which pairs with adenine instead of guanine. Alkylating agents, for example, sulphur or nitrogen mustards, ethylene oxides, ethylenemethanesulphonate and N-methyl-N'-nitro-N-nitrosoguanidine (NTG) act on guanine residues and may cause base pair deletions. Chromosomal abberations may be caused by ionising radiation such as alpha, beta and gamma rays or X-rays, or non-ionising radiation such as ultra-violet light. A variety of other chemical mutagenic compounds may also be used including diepoxides, 8-ethoxycaffeine and maleichydrazine.

Nitrate reductase deficient mutant strains may readily be identified on a medium containing chlorate (for example, 400 mmM sodium chlorate) and a non-nitrate reductase suppressing nitrogen source (such as 10 mM glutamate), since strains able to produce the nitrate reductase enzyme will reduce the chlorate to chlorite which is toxic and will kill the cells. Simple growth tests on a variety of nitrogen sources can the readily be used to distinguish nitrate reductase deficient mutants from other chlorate resistant mutants [see for instance Birkett & Rowlands, J. Gen. Microbiol., 123, p281 (1981)]. After selection on the chlorate medium, isolated mutants may also be tested for reversion of the mutation or for any loss of antibiotic titre by, for example, shake flask analysis.

Transformation of nitrate reductase deficient strains of *P. chrysogenum* and *A. chrysogenum* with a nitrate reductase marker gene will restore to the strain the ability to utilise nitrate as the sole nitrogen source.

The nitrate reductase gene to be used as the transformation marker can be isolated from a genomic DNA library of a strain of filamentous fungus. Preferably the strain will be of the same species as the intended host strain or from a strain of a related species. Thus, as well as *P.chrysogenum* and *A.chrysogenum*, strains of Aspergillus species such as *Aspergillus nidulans, Aspergillus niger* and *Aspergillus oryzae* may be used. The genomic library may be constructed by partial digestion of the total chromosomal DNA using a restriction enzyme, for example, Sau 3A1 [see for instance Garber & Yoder, Anal. Biochem., 135, p416 (1983)]. Digestion fragments in the range of 15-25 kbp are conveniently recovered for example, by size fractionation on a sucrose gradient. The digestion fragments may be ligated into a phage vector such as λEMBL3 or λEMBL4. These may then be packaged in vitro into phage particles which may then be propagated in a prokaryatic host such as *E. coli* to create a phage library. This library may be screened following plating of the phage particles on a bacterial lawn by using either all, or a fragment, of a niaD gene isolated from another filamentous fungus such a species of Aspergillus spp..

Alternatively, the library may be screened for expression of nitrate reductase activity using an expression system known in the art or one analogous to the process described herein. DNA sequences which are selected by this method may themselves be used as probes to select other DNA sequences coding for the nitrate reductase enzyme. Their effectiveness as a marker gene may be demonstrated by their use in an appropriate recombinant DNA molecule to transform nitrate reductase deficient strains of either *P. chrysogenum* or *A. chrysogenum*. The isolated DNA sequence coding for the nitrate reductase enzyme is preferably derived from the same species as that being transformed.

In the process of the invention, nitrate reductase deficient hosts are transformed with the nitrate reductase marker gene and the desired gene which are ligated into an expression vector. The expression vector is preferably one which exhibits high transformation frequency in the host strain and must be so constructed that the coding elements of the desired gene to be integrated into the genome, and the nitrate reductase marker gene, are efficiently expressed once transformed into the host.

The expression vector should be capable of replication in a prokaryotic host, preferably *Escherichia coli*, to facilitate further genetic manipulation. Following multiplication of *E. coli*, vectors containing the niaD can be readily identified using hybridisation selection, by homology to niaD genes from other related species.

Where the desired gene to be incorporated into the fungal genome is incorporated in the same expression vector as the marker gene, the desired gene should be ligated into the vector in such a way that both genes are expressed, that is the ligation does not disrupt the functional activity of the nitrate reductase gene or those genes necessary for replication and selection of the prokaryotic host. This may be achieved by ensuring that the vector possesses a unique restriction site into which the desired gene may be inserted.

Suitable expression vectors for the transformation of the nitrate reductase deficient host may consist of segments of chromosomal, non-chromosomal and synthetic DNA sequences, such as derivatives of known bacterial plasmids, for example, "natural" plasmids such as Col E1 or "artificial" plasmids such as pBR322 or pMB9, or yeast plasmids, for example, 2µ. Other suitable vectors may be phage DNA's, for example, derivatives of M13, or bacteriophage lambda, or yeast vectors such as derivatives of YIp, YEp or YRp.

Such expression vectors may also be characterised by at least one expression control sequence which is operatively linked to the nitrate reductase marker gene and the desired gene. Example of useful expression control sequences include the glycolytic promoters of yeast (e.g. the promoter for 3-phosphoglycerate kinase, PGK), the promoters of yeast acid phosphatase (e.g. Pho 5) or the alcohol dehydrogenase-2 (alcA) or glucoamylase promoter. Preferably, the control sequence is isolated with the marker gene or the desired gene thus avoiding the need to construct the expression vector using foreign control sequences.

The expression vector may also optionally be characterised by an autonomus replication sequence (ars) derived from a fragment of either mitochondrial or chromosomal DNA, preferably from the same species as that being transformed.

In order to transform the nitrate reductase deficient host cells according to the process of the invention, the cells may first be converted to protoplasts or, alternatively treated with a metal salt such as lithium acetate as described, for example, by Dhawale et al, Current Genetics, 8, p77 (1984). Other method of transformation well known in the art include electroporation of liposome-enclosed DNA treatment of protoplasts, microinjection, and alternative physical means of introducing DNA into fungal cells.

The preferred method utilises protoplasts. Prior to their formation, the host strain is cultured to a suitable population size in a conventional manner, for example, in shake flasks. The nature of the culture medium can influence the protoplast yield but will generally be conventional for the growth of *P. chrysogenum* or *A. chrysogenum* with, of course, the addition of an alternative nitrogen source to nitrate such as glutamate. Also, the maximum yield of protoplasts is obtained from the mycelium of the mutant strain during the phase of active growth. The mycelium is then recovered by filtration or centrifugation and washed to remove the culture medium. The recovered mycelium may optionally be treated with an agent to maintain thiols in a reduced state (for example dithiothreitol, 0.0005M to 0.1M at pH5 to pH8.5) to assist protoplast production and hence improve the yield.

The mycelium is then treated with one or more enzyme preparations in the presence of a suitable buffer to maintain the pH and osmotic pressure of the medium. Suitable enzyme preparations are commercially available, such as Novozym 234 or Novozym 249 (Novo, Industri, A/5 DK 2880 Bagsvaerd, Denmark). These preparations are underfined mixtures containing several enzymes such as cellulose, protease, chitinase and pectinase. The mycelium is incubated with the enzyme preparation until a satisfactory yield of protoplasts is obtained. The pH and temperature of the incubation medium should be selected in accordance with the directions for the enzyme used, for example, at about pH 5.8 and 26° C. for about 3 hours in the case of Novozym 234. Typical enzyme concentrations are in the range 0.05–20 mg/ml, for example, 5 mg/ml for Novozym 234.

A suitable buffer is, for example, 20 mM phosphate buffer, pH 5.8. The osmotic pressure of the incubation medium should be maintained in a range to ensure stability of the protoplasts, for example, equivalent to 0.5M to 1.0M. The osmotic pressure may be adjusted using inorganic salts, for example, potassium chloride or magnesium sulphate, or with sugar or a sugar alcohol.

The protoplasts may be separated from the mycelial debris by filtration through a sintered glass funnel or cotton wool and/or by centrifugation, for example, at 3000–4000 rpm for 10 to 20 minutes. The protoplasts are recovered as a pellet which should be washed in the osmotic stabilising solution (for example, 0.7M potassium chloride) before resuspending the protoplasts in an osmotically stabilised solution at a concentration of between $10^4$ and $10^8$ protoplasts/ml.

Transformation of the isolated protoplasts is effected using the vectors described above in a ratio of about 10–20 µg of vector DNA per $10^8$ protoplasts. In order maximise the probability of transformation, polyethylene glycol (PEG) is added. Preferably, the PEG has a molecular weight in the range 1000–8000, for example, about 4000. The PEG is employed as a solution in an aqueous buffer, preferably at a concentration of 20–60%, for example 50% The pH is suitably in the range 5–10, preferably between pH 5.8 and 7.5. The process is preferably assisted by calcium ions at a concentration in the range 0.002M to 1.0M, for example, using 0.05M calcium chloride. The transformation conveniently takes place at a temperature in the range of 0° to 25° C., preferably at room temperature for up to 1 hour.

Incubation may be repeated following further addition of PEG. Tranformation frequency may be improved by conducting the first incubation on ice. Also warming the transformation mixture in a water bath (about 35° C.) prior to the second incubation may improve the transformation frequency. The protoplasts may be harvested by mild centrifugation (for example, at 2000 rpm for 5 to 10 minutes) and resuspended in a little suitable osmotically stable buffer (for example, a few ml of 1.0M sorbitol).

Selection of transformants is readily achieved by plating fungal cells, which have undergone the transformation procedure, on a transformation selection medium. Such a medium should be minimal medium in which the sole nitrogen source is nitrate, such as metal nitrate salts, for example, sodium nitrate. If necessary, for instance, when protoplast transformation has taken place the medium should have a high osmotic strength to allow protoplast regeneration, for example, 11% sucrose. Incubation at between 10° and 30° C. for between 5 and 20 days is required for the transformant colonies to grow strongly out of any non-nitrate utilising background growth.

Our preferred method for transforming a nitrate reductase deficient host strain of *P. chrysogenum* or *A. chrysogenum* according to the process of the invention comprises the steps of:

(i) digestion of the total DNA isolated from cells of the same species as the intended host or a fungus of a related species, with one or more restriction enzymes, such as the enzyme Sau3A;

(ii) preparation of bacteriophage vectors known to be capable of infection of, and replication in, a chosen prokaryote, preferably *Escherichis coli*, fused with the restriction fragments obtained in (1);

(iii) In vitro packaging of the recombinant bacteriophage vectors prepared in (ii), infection of the chosen prokaryotic cells and recovery of clonal phage particles as plaques on a bacterial lawn;

(iv) screening of the recombinant cloned phage particles obtained in (iii) for the nitrate reductase gene, by homology with other known nitrate reductase genes from various species, or by functional activity;

(v) recovery of the nitrate reductase gene by subcloning suitable restriction fragments of the recombinant phage into vectors known to be capable of transformation and replication in the chosen prokaryote, preferably *E. coli;*

(vi) insertion of the desired industrially important gene, or genes particularly biosynthetic or regulatory genes involved in cephalosporin or penicillin biosynthesis, preferably by the fusion of DNA fragments with vectors obtained in (v) in such a way that both genes are expressed, that is the fusion does not disrupt the functional activity of the nitrate reductase gene or those functions necessary for replication and selection in the prokaryotic host;

(vii) as an additional, but not essential step, other component DNA fragments may also be fused to the vectors described in (v) and (vi), for examples, DNA fragments having autonomously replicating ability in yeasts or other filamentous fungi;

(viii) transformation of a nitrate reductase deficient host strain of *P. chrysogenum* or *A. chrysogenum* using the vector obtained in the prokaryotic transformants prepared as in steps (iv-vii) above and containing the industrially important gene and the nitrate reductase gene identified by the means in (iii) and (iv), such transformation preferably brought about by preparation of fungal protoplasts by enzymatic digestion of cell wall components in high osmotic strength medium and introduction of the vectors to the protoplasts by treatment with polyethylene glycol;

(ix) selection on a medium containing nitrate as the sole nitrogen source for fungal transformants expressing the newly introduced nitrate reductase gene as selectable marker, for the preferred transformation system (viii), such medium to have high osmotic strength to allow protoplast regeneration.

It will be understood that steps (ii) and (iii) may be replaced by fusion of restriction fragments directly to vectors as described in (v) and screening for niaD as in (iv). It will also be understood that the industrially important gene or genes may reside on a separate vector moiety or restriction fragment and that step (viii) can be performed as a co-transformation of the distinct vector DNA moieties, selecting for the presence of the niaD gene and screening by hybridisation or functional activity for uptake of the industrially important gene.

Transformed cells prepared according to the process of the invention may then be used in the production of penicillins or cephalosporins by fermentation. Thus in another aspect of the invention we provide for a method of producing a penicillin or a cephalosporin which comprises culturing a transformed strain of *P. chrysogenum* or *A. chrysogenum* prepared by the method of the invention as described above and isolating the desired penicillin or cephalosporin from the culture medium.

In a further aspect of the present invention, we provide vector DNA which includes a marker gene coding for nitrate reductase, said gene being operatively linked to a control sequence for expression of said gene. Preferably, the gene coding for nitrate reductase and optionally the control sequence are both derived from cells of the same species as the intended transformation host, *P. chrysogenum* or *A. chrysogenum*. A particularly preferred vector DNA contains, in addition to a marker gene coding for nitrate reductase, at least one gene, as described above, which will result in an improved strain following transformation of *P. chrysogenum* or *A. chrysogenum*.

In another aspect of the present invention, we provide transformed cells of *P. chrysogenum* and *A. chrysogenum* containing vector DNA including a marker gene coding for nitrate reductase operatively linked to a control sequence for expression of said gene within the transformed host cells.

In the following non-limiting Examples which illustrate the present invention, the following abbreviations are used: EDTA—ethylenediaminetetraacetic acid; EGTA—ethyleneglycol-bis-($\beta$-aminoethyl ether)N,N'-tetraacetic acid; SDS—sodium dodecyl sulphate; Tris-HCl—tris(hydroxymethyl) aminomethane hydrochloride; DTT—DL-dithiothreitol; ATP—adenosine triphosphate; SSC—saline sodium citrate; PEG—polyethylene glycol; SSPE—saline sodium phosphate/EDTA; kb—kilobase pairs of DNA.

EXAMPLE 1

Heterologous Transformation System, Based Upon the Use of Nitrate Reductase Genes from Related Fungi in *Penicillium chrysogenum*

Step 1: Isolation of *Aspergillus nidulans* niaD Gene-Specific Probe

Plasmid pNllA was isolated from an *A. nidulans* gene library constructed in the argB gene-based cloning vector plLJ16 (Johnstone et al, EMBO J. 4, (1985), 1307-1311 by its ability to complement a niiA4 (nitrite reductase gene), argB2 double mutant strain. Further complementation experiments with a number of genetically identified deletions extending into the niaD gene (nitrate reductase gene) have shown that pNllA contains the entire crnA gene (nitrate permease) and part of niaD. The position of the niiA-complementing DNA fragment of pNllA relative to a restriction map of the niiA and niaD gene region is illustrated in FIG. 1. This map is illustrative only, in that a limited number of restriction sites are shown and in some instances, not all sites of a particular restriction enzyme have been mapped.

DNA of pNllA was digested with EcoRl and religated to construct the plasmid pSTA1. This treatment provided a means of deleting all the DNA to one side of the EcoRl site (illustrated in FIG. 1) and thus removing all crnA and niiA gene encoding sequences. A 2.4 kb Xbal fragment from within the pSTA1 DNA contains part of the niaD gene and thus provides a means of screening further isolated clones for the presence of an intact niaD gene. The plasmid pSTA1 was deposited under the terms of the Budapest Treaty on the international Recognition of the Deposit of Micro-organisms for the Purposes of Patent Procedure, at the National Collection of industrial and Marine Bacteria, 135 Abbey Road, Aberdeen, AB9 8DG on 23rd January 1989 under the Accession number NClB 40102.

A 10 ug aliquot of pSTA1 DNA was brought to 1x Xbal buffer conditions (10 mM Tris-HCl, pH 7.5, 7 mM Mgcl$_2$, 100 mM NaCl, 7 mM 2-mercaptoethanol) and digested with 100 units Xbal enzyme (Amersham, International Plc, White Lion Road, Amersham, Bucks, HP7 9LL). The restriction products were resolved on a 1% low melting temperature agarose gel (Sigma Chemical Co, Fancy Rd, Poole, Dorset, BH17 7NH) by electrophoresis under standard conditions. The DNA band containing the 2.4 kb Xbal fragment was excised, remelted at 42° C. and the DNA recovered by phenol extraction and ethanol precipitation. This material was used as a niaD-specific probe in order to isolate an intact, functional niaD gene.

Step 2: *Aspergillus nidulans* DNA Library Construction

AN *A nidulans* strain proficient in nitrate utilization was grown at 28° C. in Aspergillus Complete Medium, ACM (Clutterbuck, in Handbook of Genetics (King, Ed.) pp 447-510 Plenum Press, 1974). Suitable strains are widely available from various fungal culture collections, e.g.: American Type Culture Collection (ATCC) 12301 Parklawn Drive, Rockville, Md. 10852, USA; Commonwealth Mycological Institute, Ferry Lane, Kew, Surrey, TW9 3AF; Fungal Genetics Stock Centre, California State University, Humboldt, Arcata, Calif. 95521, USA.

Mycelium was harvested after overnight growth by filtration, frozen in liquid nitrogen and lyophilised overnight. This material was used to isolate high molecular weight DNA using a modification of the method of Raeder and Broda (Lett. Applied Microbiol. 1 (1985), 17-20). The lyophilised mycelium (2.5 g) was ground with 0.1 volumes of sand and rehydrated in 5 ml of an extraction buffer consisting of 25 mM EDTA, 0.5% SDS and 250 mM NaCl in 200 mM tris-HCl, pH 8.5. A 3.5 ml aliquot of phenol (equilibrated with extraction buffer) was added and mixed, followed by 1.5 ml chloroform/isoamyl alcohol (24:1) then the solution was vortexed. The lysate was centrifuged at 12000 g for one hour at room temperature, then nucleic acids were precipitated from the aqueous phase with 0.6 vol propan-2-ol. The loose pellet obtained on standing was washed in 1 ml 70% ethanol and raised in 1 ml TE buffer (10 mM Tris-HCl pH 8.0, 1 mM EDTA). RNA was precipitated by the addition of 7.5M ammonium acetate to 2.5M and incubation at 4° C. for 15 minutes. After a brief centrifugation, as above, DNA was precipitated from the aqueous phase with 2 vol ethanol. The pellet was washed in 70% ethanol, dried and raised in 1 ml TE buffer in about 1 mg yield.

The DNA, obtained as above was partially restricted with the enzyme Sau3Al (Amersham International Plc). A 200 ug aliquot was adjusted to 133 Sau3Al buffer conditions (10 mM Tris-HCl, pH 7.5, 7 mM MgCl$_2$, 20 mM NaCl) in a 500 ul volume, then digested with 1.5 units enzyme for 1 hour at 37° C. The reaction was terminated by the addition of EDTA to 10 mM and then the reaction products size fractionated through a preformed 38 ml sucrose gradient (10-40% sucrose in IM NaCl, 5 mM EDTA, 20 mM Tris-HCl pH 8.0) centrifuged for 20 h at 90000 g and 21° C. in an SW28 rotor (Beckman Instruments (UK) Ltd, Progress Rd, High Wycombe, Bucks, HP12 4JL). The gradient was fractionated into 0.5 ml aliquots and DNA of size range 15 kb-25 kb (as determined by agarose gel electrophoresis) was pooled, adjusted to 0.3M in sodium acetate and precipitated in ethanol by addition of 2 volumes ice-cold ethanol and incubation on ice for 30 minutes. The DNA pellet recovered by centrifugation was raised in 25 ul TE buffer.

The lambda cloning vector λEMBL3 (Frischauf et al, J. Mol. Biol. 170: (1983) 827-842) was obtained as BamHl digested arms from Stratagene Inc. (11099 North Torrey Pines Rd. La Jolla, Calif. 92037, USA), The Sau3Al fragments of *A. nidulans* DNA (1 ug) and λEMBL3 arms (2 ug) were mixed in 20 ul ligation buffer (20 mM Tris-HCl, pH 7.6, 10 mM MgCl$_2$, 10 mM DTT, 0.6 mM ATP) and incubated at 14° C. for 18 hours with 5 units T4 DNA ligase (Amersham).

The ligation products were packaged in vitro into phage particles using the commercially available Gigapack Kit (Stratagene Inc). The packaged phage were propagated in the *E. coli* strain Q358, creating a recombinant phage library of $1.5 \times 10^6$ plaque forming units (pfu).

Step 3: Isolation of a Functional *Aspergillus nidulans* niaD Gene Clone

Approximately $3 \times 10^4$ pfu of the *A. nidulans* recombinant phage library were mixed with $1 \times 10^8$ *E. coli* Q358 cells in 0.5 ml 10 mM MgSO$_4$. After 15 minutes incubation at 37° C. the mixture was added to 25 ml molten (42° C.) soft agar (LB+10 mM MgSO$_4$+0.6% agar) and used to overlayer a $20 \times 20$ cm petri plate containing LB medium +10 mM MgSO$_4$. (LB (Luria-Bertani) medium contains 1% Bacto-tryptone, 0.5% yeast extract, 0.5% NaCl at pH 7.0. Standard techniques for handling *E. coli* are described by Maniatis et al, Gene Cloning. A Laboratory Manual, Cold Spring Harbor Lab, New York, 1982). Following overnight incubation, duplicate filter impressions of the plate were taken using Hybond-N membranes (Amersham) by standard techniques.

The filters were each incubated in 25 ml of prehybridisation buffer (6×SSC, 5× Denhardt solution, 0.5% sodium dodecyl sulphate (SDS) and 500 ug denatured salmon sperm DNA at 65° C. for 6 hours. SSC is 0.15M NaCl, 0.015M sodium citrate; Denhardt solution is 0.02% of each of polyvinylpyrrolidone, bovine serum albumin, ficoll (Sigma Chemical Co).

The 2.4 kb Xbal fragment of pSTA1 (a niaD-specific DNA fragment), prepared as in step 1, was labelled with $^{32}P$ by the method of nick-translation using a commercially available kit (Amersham). The radioactively-labelled fragment was recovered free from unincorporated label by elution from a Sephadex G-50 Nick Column (Pharmacia LKB Biotechnology, Midsummer Boulevard, Milton Keynes, Bucks MK9 3HP) and added to fresh 25 ml aliquots of hybridisation buffer (prepared as for prehybridisation buffer). Hybridisation was at 65° C. overnight. The filters were then washed free of excess probe using standard conditions to a final wash of 0.1×SSC, 0.1% SDS at 65° C. and the dried filters exposed to X-ray film (Hyperfilm B-max, Amersham) at −20° C. for 4 days.

Putative positive plaques were picked and reprobed at a lower plating density (approximately 100 plaques per 9 cm diameter plate). One positive clone (λANBa) isolated in this way was retained for further use. This clone encodes the entire niaD gene of *A. nidulans* as illustrated in FIG. 1, and is a source of exogenous DNA for our transformation protocol.

Step 4: Isolation of a Functional *Aspergillus niger* niaD Gene Clone

A nitrate utilizing *A. niger* strain was grown in complete medium essentially as described in Step 2. Suitable strains are widely available through ATCC, CMI, FGSC or other culture collections. The mycelium was harvested and DNA isolated by the method described in Step 2.

Southern blotting of *A. niger* genomic DNA using the 2.4 kb Xbal fragment of pSTA1 as a niaD-specific probe revealed that the *A. niger* nitrate reductase (niaD) gene resides on DNA fragments of about 2.8 and 2.0 kb when digested with EcoRl. Experimental conditions for hybridisation and production of $^{32}P$-labelled probe were essentially as described in Step 3. Background, non-hybridised radioactivity was removed by washing to a final salt concentration of 2×SSC at 56° C.

*A. niger* genomic DNA (50 ug) was brought to 1×Sau3A1 buffer buffer conditions and digested with 2 units Sau3A1 at 37° C. for 30 minutes in a 200 ul volume, Fragment in the range 6–12 kb were isolated from a 1% agarose gel by centrifugation through nitrocellulose (Zhu et al, Biotechnol. 3 (1985), 1014–1016).

A 2 ug DNA aliquot of the widely available plasmid vector pUC8 (Vieira and Messing, Gene 19 (1982), 259–268) was adjusted to 1× BamHl buffer conditions (10 mM Tris-HCl pH 8.0, 7 mM MgCl$_2$, 100 mM NaCl, 2 mM 2-mercaptoethanol) and digested with 10 units BamHl at 37° C. for 2 hours in a 10 ul volume. DNA was precipitated by addition of ammonium acetate to 2M and 2 volumes of cold ethanol. The DNA pellet recovered by centrifugation was raised in 20 ul of 50 mM Tris-HCl pH 8.0, 0.1 mM EDTA and incubated with 0.5 units of Alkaline Phosphatase (Boehringer Mannheim GmbH, PO Box 310 120, D-6800, Mannheim 31 FRG) at 37° C. for 1 hour. The phosphatase was inactivated by addition to EGTA to 10 mM and heating to 65° C. for 45 minutes. The DNA was precipitated by addition of sodium acetate to 0.3M and 2 volumes of cold ethanol.

Aliquots containing approximately 250 ng of the *A. niger* Sau3A1 fragments and 100 ng of the dephosphorylated BamHl cut pUC8 vector were mixed and ligated essentially as described in Step 2. The ligation products were used to transform the widely available *E. coli* strain DH5 to produce an A. niger DNA library of around 2×10$^4$ clones enriched for fragments expected to carry the nitrate reductase structural gene. The library was divided into 9 pools each containing approximately 1500–3000 individual clones. The pooled isolates were grown in LB medium supplemented with 100 ug/ml ampicillin and DNA isolated by a modification of the alkaline SDS method of Birnboim and Doly (Maniatis et al, loc cit). The isolated DNA was digested with EcoRl and Bamhl, resolved by electrophoresis, blotted and probed with $^{32}P$-labelled niaD-specific 2.4 kb Xbal fragment of pSTA1, isolated as described in Step 1. One of the pools contained fragments which showed strong homology to this probe. This pool was used to isolate niaD-specific clones by standard colony hybridisation as described by Maniatis et al (loc. cit.), again using the pSTA1 DNA fragment as probe. Two clones were isolated by this means. One of them was subsequently used in other tests and is designated pSTA10. A restriction map of pSTA10 (FIG. 2) illustrates the approximate location of the niaD gene relative to the *A. niger* DNA fragment present in pSTA10. This map is intended to be illustrative only, in that a limited number of restriction sites are shown and in some instances not all sites of a particular restriction enzyme have been mapped.

Step 5: Isolation of a Functional *Aspergillus oryzae* niaD Gene Clone

A genomic DNA library of the *A. oryzae* strain ATCC 91002 was prepared in the λEMBL3 vector as described in step 2. The initial phage library contained about 1×10$^5$ pfu. About 4×10$^4$ were propagated in a widely available *E. coli* strain NM 259 and screened for the presence of niaD gene sequences by hybridisation as described in step 3. The 2.4 kb Xbal fragment of pSTA1 containing part of the *A. nidulans* niaD gene, isolated as described in step 1, was used as the hybridisation probe. Two clones were identified as containing niaD gene sequences by this means. One of these designated λSTA62 was used for further subcloning work.

Approximately 5 ug of DNA isolated from λSTA62 was adjusted to 1×SalI buffer conditions (10 mM Tris-HCl, pH 8.0, 150 mM NaCl, 10 mM MgCl$_2$, 1 mM 2-mercaptoethanol) and digested with 50 units SalI at 37° C. for 2 hours in a 50 ul reaction volume. The digest fragments were resolved on an 0.8% agarose gel and an 8.2 kb fragment was isolated as described in step 4. This fragment was known to carry the *A. oryzae* niaD gene by virtue of homology with the *A. nidulans* niaD gene probe.

A 1 ug aliquot of the widely available plasmid vector pUC18 (Yanisch-Perron et al, Gene 33 (1985), 103–119) was similarly digested with 10 units SalI. Approximately 100 ng quantities of the isolated 8.2 kb *A. oryzae* SalI fragment and the SalI-digested pUC18 were ligated using 1 unit T4 DNA ligase as described in step 2. The ligation products were used to transform the widely available *E. coli* strain DH5. Ampicillin resistant colonies were screened for the presence of plasmids containing the required insert DNA using the modified alkaline SDS method of Birnboim and Doly as described by Maniatis et al (loc. cit.). A plasmid isolate carrying the 8.2 kb SalI fragment from λSTA62 was identified and designated pSTA14. A restriction map of the *A. oryzae* DNA present in pSTA14 is shown in FIG. 3. The map is intended to be illustrative only, in that a limited number of restriction enzyme sites are shown and in some instances not all sites of a particular restriction enzyme have been mapped.

Step 6: Isolation of *Penicillium chrysogenum* niaD⁻ Mutants

The *P. chrysogenum* strain Q176 (ATCC 10002) was grown on Aspergillus Complete Medium (Clutterbuck, loc. cit) supplemented with 10 mM $NH_4Cl$ and solidified with 1.5% agar. Conidia were harvested by suspension in 0.01% Tween 80. Approximately $10^8$ conidia were spread plated on to chlorate selection medium based upon Aspergillus Minimal Medium, AMM (Clutterbuck, loc. cit) supplemented with 6 mM L-arginine and 94 mM $NaClO_3$ as described (Birkett and Rowlands, J. Gen. Microbiol. 123 (1981): 281–285). The basis of this chlorate selection for mutants unable to utilise nitrate as sole nitrogen source is well documented and is reviewed by Cove, Biol. Revs. 54 (1979), 291–327.

Colonies which grew strongly were picked and purified as examples of spontaneously occurring chlorate-resistant mutants. Isolates were tested for reversion to nitrate utilisation by plating conidia on AMM containing 2 mM sodium nitrate and scoring growth. Those with a reversion rate of less than $10^{-8}$ nitrate proficient isolates/input conidia were further tested for growth on a variety of nitrogen sources (Birkett and Rowlands, loc. cit). Those which grew on nitrite (1.5 mM) or adenine (0.6 mM adenine hydrochloride) but failed to grow on nitrate were deemed to be nitrate reductase gene mutants and termed niaD⁻ (by analogy to the *A. nidulans* criteria).

These isolates were further tested for nitrate reductase enzyme activity using the biochemical method of Cove (Biochim. Biophys. Acta, 113 (1966), 51–56). Mycelium was grown in AMM broth supplemented with 20 mM $NaNO_3$ for 26 hours at 26° C., 290 rpm for these assays. The isolates of the niaD type showed minimal nitrate reductase activities in these assays, while Q176 contained normal levels of the enzyme.

A strain designated S1900 is an example of such a spontaneously occurring niaD⁻ mutant and was deposited at the Commonwealth Mycology Institute Culture Collection, under the terms of the Budapest Treaty on Jan. 23, 1989 under the Accession number CMICC 330177.

Step 7: Preparation of *Penicillium chrysogenum* Protoplasts

Approximately $10^8$ conidia of the mutant S1900 were grown in 100 ml ACM for 42 hours at 26° C. with shaking (220 rpm). The mycelium was recovered by filtration on to Whatman No. 1 paper, then resuspended in 0.7 M KCl, 10 mM phosphate buffer pH 5.8 containing Novozym 234 (Novo Industri, A/S DK2880 Bagsvaerd, Denmark ( at 10 mg/ml. This buffer is added at a rate of 10 ml/gram wet weight cells. The cell suspension is incubated at 26° C. with gentle shaking for 2 hours, then protoplasts separated from the bulk of mycelial debris by filtration through a sintered funnel (porosity 2). Protoplasts were recovered by centrifugation at 4000 rpm for 10 minutes in a bench top centrifuge. The protoplast pellet was washed twice in 5 ml 0.7 M KCl, 50 mM $CaCl_2$ buffer, recovered and finally resuspended to a density of about $5 \times 10^8$ protoplasts/ml in $KCl/CaCl_2$ buffer.

Step 8: Transformation of S1900 Protoplasts

A 500 ul aliquot of S1900 protoplasts prepared as in step 7 was mixed in a 1.5 ml polypropylene tube with 10–30 ug DNA (in TE buffer) of λAN8a, pSTA10 or pSTA14. An equal volume of 50% polyethylene glycol (PEG-4000, Sigma Chemical Co) in 0.7 M KCl, 50 mM $CaCl_2$, 10 mM Tris-HCl, pH 7.5, was added and the mixture held on ice for 30 minutes. The mixture was then diluted to 1.5 ml with $KCl/CaCl_2$ buffer and aliquots spread on to AMM agar supplemented with 20 mM $NaNO_3$ as sole nitrogen source and 0.7 M KCl as osmotic stabiliser.

The plates were incubated at 26° C. for 7–10 days to allow nitrite-utilising transformants to grow out of the background of nitrate non-utilising material. The frequency of transformation was approximately 10 transformants per ug exogenous DNA when using the *A nidulans* niaD gene clone λAN8a or the *A. niger* gene clone λSTA10, but only about 2 transformants/ug DNA of the *A. oryzae* gene clone pSTA14. The S1900 transformant isolates generally showed improved sporulation ability and distinctly altered colony morphology.

The transformation of S1900 was also confirmed by Southern blotting using standard methodology as described by Maniatis et al. (loc. cit.) and hybridization of the genomic DNA of transformant isolates with $^{32}P$-labelled fragments of λAN8a, pSTA10 or pSTA14 DNA. The labelling of the probe fragments was essentially as described in step 3. Hybridisation conditions were; $5 \times SCC$, $5 \times Denhardts$ solution, 50 mM phosphate buffer pH 6.5, 20 ug/ml sonicated herring sperm DNA. Blots were washed at 65° C. by several stages from $5 \times SSC$ to a final salt concentration of $0.1 \times SSC$ in the presence of 0.1% SDS.

Analysis of transformants by these techniques revealed that the exogenous DNA of either λAN8a, pSTA10 or pSTA14 had integrated into the *P. chrysogenum* S1900 recipient genome. Restriction analysis showed that the integration site was different in each of the transformants and that the number of integration events could vary in each transformant.

EXAMPLE 2

Homologous Transformation System for *Acremonium chrysogenum* Based upon the Native Nitrate Reductase Gene Step 1: Isolation of the *Acremonium chrysogenum* Nitrate Reductase Gene

*A. chrysogenum* strain M8650 (ATCC 14553) was grown in the defined liquid medium of Demain, as described by Queener et al (Microbiology, 1985, Leive L Ed., pp. 468–472. American Society for Microbiology, Washington, DC, 1985). The mycelium was harvested and high molecular weight DNA isolated as described in Step 2 of Example 1.

An M8650 genomic library was constructed by ligating partial Sau3A1 digestion fragments (15–20 kb) into the BamHI cloning site of λEMBL3 using standard techniques (Maniatis et al loc. cit.), as described in Step 2 of Example 1. The in vitro packaged recombinant phage particles (about $1.3 \times 10^5$ pfu) were propagated in the widely available E. coli strain NM259 to give an amplified library of around $1 \times 10^{10}$ pfu/ml. For screening, 12 plates (9 cm diam) each containing about $2 \times 10^4$ pfu were prepared using standard methodology (Maniatis et al, loc cit). Duplicate filter impressions of each plate were taken on nitrocellulose membranes. Filters were prehybridised for about 4 hours at 56° C. in the following prehybridisation buffer at about 4 ml buffer per filter; $5 \times SSPE$ (0.9M NaCl, 50 mM $NaH_2PO_4$, 5 mM EDTA), 6% PEG6000, 0.5% dried milk powder, 1% SDS, 0.15% $Na_4PO_7$, 250 ug/ml sonicated herring sperm DNA.

The library was screened with the 2.4 kb Xbal fragment from within the A. nidulans nitrate reductase gene. This fragment was isolated as described in Step 1 of Example 1. Isolated fragment (25 ng) was radioactively labeled with $^{32}P$ using Klenow polymerase with random priming from mixed hexamer oligonucleotides (Multiprime Kit, Amersham) following the manufacturers guidelines. The library filters were hybridised overnight at 56° C in fresh prehybridisation buffer containing the radioactive probe. Background radioactivity from non-hybridised probe was removed by washing twice at 56° C. for 20 minutes in a buffer containing $5 \times SSC$, 0.1% SDS, 0.1% SSPE (approximately 10 ml/filter) then twice at 56° C. for 20 minutes in $3 \times SSC$, 0.1% SDS, 0.1% SSPE. The washed filters were exposed to X-ray photographic film for 3 days at $-70°$ C. with intensifying screens.

A number of putative positive plaques were identified. They were plaque purified and re-tested during two further rounds of hybridisation screening. Two strongly positive clones were confirmed by this procedure. One of these, termed λSTA6, was used in subsequent work. An 8.8 kb EcoRI fragment present within λSTA6 is of the same size as an EcoRI fragment of M8650 genomic DNA identified by Southern blotting as being homologous to the 2.4 kb Xbal fragment containing part of the A. nidulans niaD gene.

A phage stock of λSTA6 was prepared and DNA isolated using standard methodology (Maniatis et al. loc cit). Approximately 5 ug of λSTA6 DNA was digested with 25 units EcoRI in a 50 ul reaction containing 100 mM Tris-HCl pH 7.5, 7 mM $MgCl_2$, 50 mM NaCl, 7 mM 2-mercaptoethanol at 37° C. for 2 hours. The digestion products were resolved by electrophoresis on a 0.8% agarose slab gel. The 8.8 kb fragment was recovered by the sodium iodide-glass method (Vogelstein and Gillespie, Proc. Natl. Acad. Sci. U.S.A. 76 (1979), 615–619) using a commercially available kit (Geneclean; Bio 101 Inc, PO Box 2284, La Jolla, Calif. 92038, U.S.A.).

A 1 ug aliquot of plasmid pUC18 was similarly digested with 10 units EcoRI. Approximately 100 ng quantities of the 8.8 kb EcoRI fragment of λSTA6 and EcoRI digested pUC18 were ligated using 2.5 units T4 DNA Ligase as described in Step 2 of Example 1. The ligation products were used to transform E. coli strain DH5. Ampicillin resistant colonies were screened for the presence of plasmid DNA using the alkaline SDS lysis method as described by Maniatis et al (loc cit). A plasmid isolate carrying the 8.8 kb EcoRI fragment from λSTA6 was identified and termed pSTA700. A restriction map of the A. chrysogenum DNA portion of pSTA700 is shown in FIG. 3. This map is intended to be illustrative only, in that a limited number of restriction enzymes have been used and in some instances not all sites of a particular restriction enzyme are shown. The map is presented as an aid to discussion. The plasmid pSTA700 was deposited in the National Collection of Industrial and Marine Bacteria under the terms of the Budapest Treaty on 23rd January 1989 under the Accessio number NCIB 40103.

Confirmation of the present of the niaD gene within pSTA700 was obtained by Southern blotting performed as described above. The pSTA700 plasmid was used to probe A. chrysogenum genomic DNA digested with EcoRI, BglII or BamHI. This probe gave identical banding patterns in these digests to those obtained when using the 2.4 kb Xbal fragment of pSTA1 as probe, i.e.: an EcoRI fragment of 8.8 kb, BamHI fragments of 8.0 and 3.8 kb and BglII fragments of 6.4, 2.5 and 1.3 kb. This confirms the presence of A. chrysogenum DNA associated with the niaD gene within the pSTA700 plasmid, and also shows that no gross rearrangements have occurred during the cloning process. The niaD gene was further localised within pSTA700 by Southern blotting. The probe used in this case was a 124 by PstI-AccI fragment of the A. nidulans niaD gene. This fragment contains a region of the niaD gene which is highly conserved among fungal and plant nitrate reductase genes. The location of this fragment is indicated in FIG. 1. A 5 ug aliquot of pSTA1 DNA was digested with 10 units PstI and 10 units AccI in a 50 ul reaction volume containing 10 mM Tris-HCl pH 7.5, 7 mM $MgCl_2$, 60 mM NaCl, 7 mM 2-mercaptoethanol at 37° C. for 2 hours. The digestion products were resolved by electrophoresis on a 2% agarose gel and the 124 bp fragment recovered using Geneclean. The fragment was radioactively labelled with $^{32}P$ using the random priming method. Prehybridisation, hybridisation and filter washing were as described above. The Southern hybridisation experiment revealed a 1.3 kb BglII fragment of pSA700 with homology to the niaD-specific probe fragment.

Step 2: Isolation and Characterisation of Nitrate Reductase Gene Mutants of Acremonium chrysogenum A. chrysogenum M8650 mycelium was grown in Demains medium for 5–8 days at 28° C. with shaking (2202 rpm). Conidiospores were obtained by vacuum filtration through a sterile Whatman no 1 filter paper in a Buchner funnel. The filtrate was collected in a sterile flask and conidia recovered by centrifugation. A 100 ml culture of M8650 yielded around $2 \times 10^{10}$ conidia by this method. Conidia are stored in aliquots over liquid nitrogen using 10% methanol as cryopreservative.

Approximately $10^8$ non-mutagenised conidia, were spread plated at around $10^7$ conidia/plate onto Aspergillus minimal media. AMM (Clutterbuck loc cit, as described in Step 6 of Example 1) supplemented with 10 mM glutamate and 470 mM sodium chlorate. After 12–14 days incubation at 28° C., spontaneous chlorate resistant mutants were isolated. Initial characterisation of the mutants was carried out using simple nitrogen growth tests described by Birkett and Rowlands (loc cit). The nirA, crnA and areA type mutants could be distinguished from niaD and cnx mutants (A. nidulans gene designations are used as standard). These growth tests could not readily distinguish niaD and cnx-type mutants as *A. chrysogenum* failed to grow on hypoxanthine (unlike *A. nidulans*) or adenine (unlike *P. chrysogenum*). A simple phenotypic assay to distinguish niaD and cnx type mutants was developed using alternative purines as sole nitrogen source. When using quinic acid (1%) as carbon source and inosine (2 mM) as nitrogen source in a medium based on AMM, niaD mutants were found to grow, while cnx mutants could not.

The phenotypes assigned to niaD or cnx mutants were further confirmed by enzyme assays. A cnx mutant should lack purine hydroxylase I enzyme activity since this enzyme requires a molybdenum-containing cofactor which is also a common requirement for nitrate reductase activity. Purine hydroxylase I catabolises hypoxanthine to xanthine to uric acid (Lewis et al, Euro. J. Biochem. 91 (1978), 311-316). The assay for purine hydroxylase I was performed essentially as described by Mendel and Muller (Biochem. Physiol. Plantzen, 170 (1976) 538-541). In brief, *A. chrysogenum* M8650 and putative niaD or cnx mutants were grown in liquid Aspergillus Complete Medium (Clutterbuck, 1974 loc. cit.) for 24 hours at 28° C., 220 rpm harvested by centrifugation, resuspended in liquid AMM supplemented with 500 mM acid and incubated for a further 3.5 hours at 28° C., 290 rpm. The mycelium was harvested, ground to a fine powder in liquid nitrogen and extracted into 0.1M potassium phosphate buffer pH 7.5 containing 1mM EDTA, 10 mM 2-mercapoethanol, 1% Triton X-100 at 2 ml buffer/g wet weight mycelium. After centrifugation at 20000 rpm in a SW27 rotor (6×14 ml tubes, Beckman Instruments) for 20 minutes at 4° C., the extracts (100 ul aliquots) were loaded on to a non-denaturing 7% polyacrylamide tube gels prepared by standard techniques (for example see Hames and Rickwood, Gel Electrophoresis of Proteins. A Practical Approach. IRL Press, London, 1981). After electrophoresis at 5 mA until the bromophenol blue tracking dye reached the bottom of the gel, the gel was stained for purine hydroxylase I activity in the dark in 0.1M sodium pyrophosphate buffer, pH 8.0, containing 2 mM hypoxanthine, 1 mM nitrotetrazolium blue (Sigma Chemical Co), 0.1 mM phenazine methosulphate (Sigma). Some of the isolates tested were found to lack purine hydroxylase activity by this test and were assigned as cnx mutants. To further characterise niaD mutants, isolates were also tested for the nitrate reductase enzyme property of NADPH-linked cytochrome C reductase activity using the methods described by Cove and Coddington (Biochim. Biophys. Acta, 110 (1965), 312-318) and Wray and Filner (J. Biochem. 119 (1970), 715-725). Isolates which retained purine hydroxylase I activity but with greatly reduced levels of NADPH-linked cytochrome C reductase activity were assigned as niaD mutants. The isolates with reduced purine hydroxylase I activity showed wild type levels of NADPH-linked cytochrome C reductase activity consistent with them being cnx mutations.

The niaD mutants were screened for rates of reversion to nitrate utilization as described in Step 6 of Example 1. Stable mutants were identified as having reversion frequencies of less than $10^{-8}$ reverants/condiospore. One of these isolates, designated as *A. chrysogenum* strain M1160 was used as a suitable recipient for transformation by vectors containing intact niaD genes. This strain was deposited in the Commonwealth Mycological Institute Culture Collection under the terms of the Budapest Treaty on 23rd January 1989 under the Accession number CMICC330178.

Step 3: Preparation of Protoplasts from *Acremonium chrysogenum*

The strain M1160 was grown from a conidial inoculum (about $10^8$ conidia) in 100 ml Demains medium (Queener et al, loc cit) for around 40 hours at 28° C. with shaking at 290 rpm. Mycelium was harvested in sterile muslim, washed with distilled water and resuspended in 0.1M citrate-phosphate buffer, pH 7.1, 10 mM dithiothreitol at 50 ml buffer per gram wet weight mycelium. This was gently shaken for 30 minutes at 28° C., then the mycelium was recovered and resuspended in 0.1M citrate-phosphate buffer, pH 5.8 containing, 0.7M KCl, 5 mg/ml Novozyme 234 (Novo Industri) at 50 mg/g mycelium. The material was incubated for a further 60 minutes at 28° C. with gentle shaking.

The resultant protoplasts were harvested through a sintered glass funnel (porosity 1) under slight vacuum and collected by pelleting at 3000 rpm for 10 minutes. The pellet was washed 3 times in 0.7M KCl, then resuspended at a concentration of around $1 \times 10^9$ protoplasts/ml.

Step 4: Transformation of M1160 Protoplasts

Aliquots of 100 ul protoplast suspension were transferred to 1.5 ml polypropylene tubes and $CaCl_2$ was added to 50 mM final concentration. A 10 ug quantity of DNA of either λSTA6 or pSTA700 in a volume of less than 20 ul TE buffer, and 10 ul PEG solution (50% PEG 4000 (Sigma Chemical Co), 50 mM $CaCl_2$, 10 mM Tris-HCl, pH 7.5) were added and mixed by hand. Control samples were also set up with no exogenous DNA present. The mixtures were incubated at room temperature for 20 minutes before a further 900 ul PEG solution was added. After 20 minutes incubation the protoplast mixtures were spread in 0.1 ml aliquots or minimal medium plates (AMM, supplemented with 10 mM $NaNO_3$ as nitrogen source and 11% sucrose as osmotic stabiliser). The plates were incubated at 28° C. for up to 21 days. Transformant colonies usually grew strongly out of a faint background growth within about 10 days.

The basic procedure described above routinely yields about 2-4 transformants/ug DNA, pSTA700 DNA giving slightly greater transformation frequencies than λSTA6. Modifications of the transformation protocol give improved frequencies, namely:

(i) Cold Shock: The first 20 minute incubation of protoplasts, DNA and PEG solution is carried out on ice. This results in transformation efficiencies of around 6-7 transformants/ug DNA.

(ii) Heat Shock: The mixtures are transferred to a water batch at 35° C. for 2 minutes after the first 20 minutes incubation, before addition of the 900 ul of PEG solution. This results in transformation frequencies of around 9-10 transformants/ug DNA.

As in Step 8 of Example 1, transformant colonies were purified by subculture on minimal medium supplemented with nitrate. Uptake of exogenous DNA was proved by Southern blotting of the transformant genomic DNA, using the input vector DNA, either λEMBL3 or pUC18, as hybridisation probe. The hybridisation conditions and probe preparation were as described in steps 3 and 8 of Example 1.

BRIEF DESCRIPTION OF THE DRAWINGS

As referenced in the accompanying text, the following drawings are included.

The niaD structural gene is indicated by the position of the hatched area with the direction of transcription shown by the arrow. The bars represent the portions of this region present in the recombinant constructs described in the test. The XbaI, PstI and AccI sites highlighted (*) delimit fragments used as hybridisation probes (see text).

Figure 1:
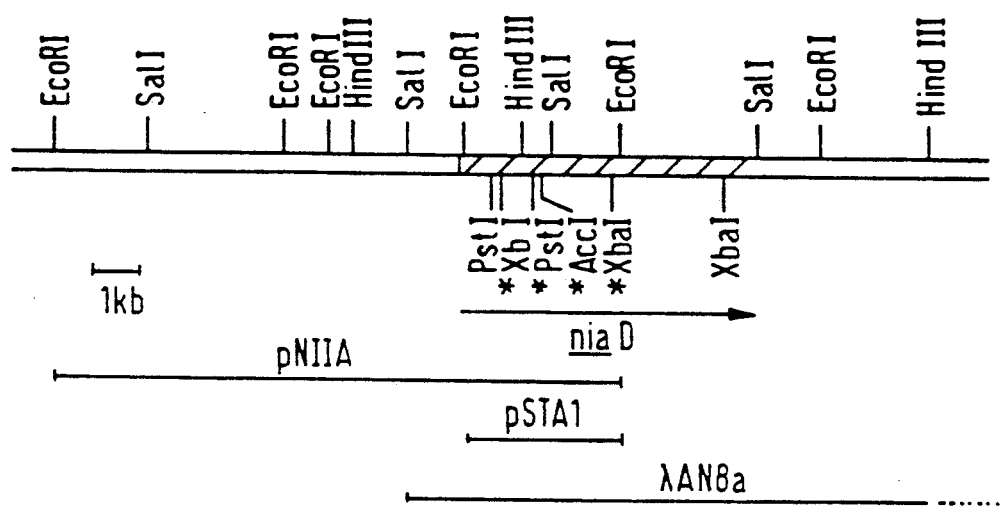
FIG. 1: Restriction Map of the *Aspergillus nidulans* niaD Gene Locus
Figure 2:
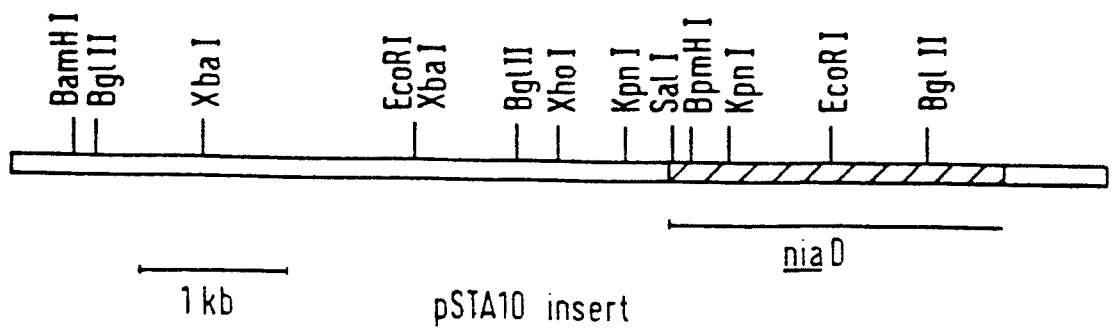

FIG. 2: Restriction Map of the *Aspergillus niger* niaD Gene Locus

The map represents the fragment of *A. niger* DNA carried by the plasmid pSTA10. The niaD structural gene is indicated by the position of the hatched area. The direction of transcription was deduced by hybridisation to 5' and 3' end specific probes from the *A. nidulans* niaD gene.

Figure 3:
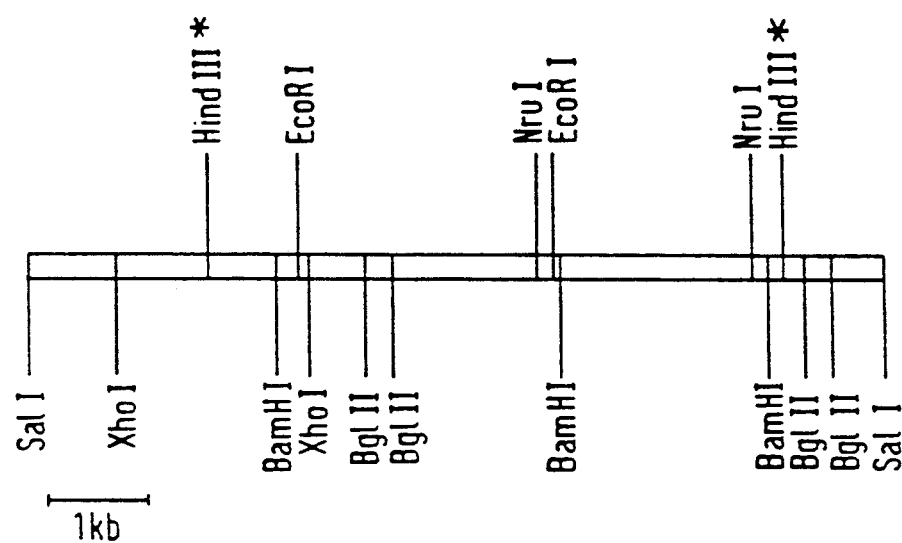

FIG. 3: Restriction Map of the *Aspergillus oryzae* niaD Gene Locus

The map represents the 8.2 kb SalI fragment of *A. oryzae* DNA carried by the plasmid pSTA14. The niaD structural gene is positioned within the 5.5 kb HindIII fragment as indicated (*).

Figure 4:
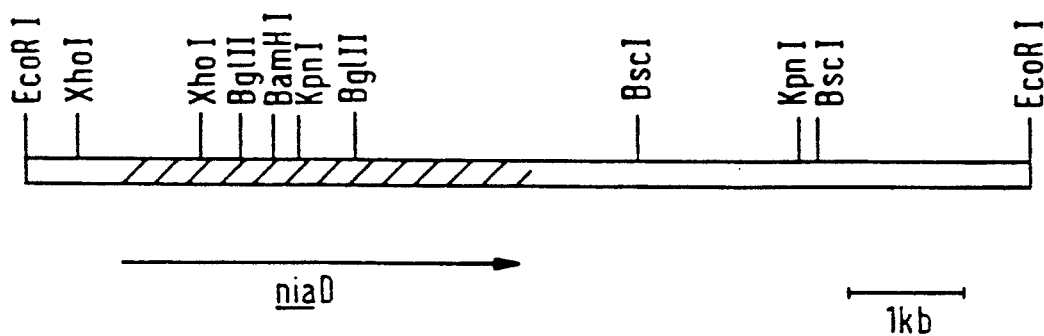

FIG. 4: Restriction Map of the *Acremonium chrysogenum* niaD Gene Locus

The map represents the 8.8 kb EcoR1 fragment of *A. chrysogenum* DNA carried by the plasmid pSTA700. The niaD structural gene location is indicated by the hatched area. The direction of transcription (arrowed) was deduced from DNA sequence analysis and comparison to the *A. nidulans* niaD gene.

We claim:

1. Vector DNA for the transformation of cells of *P. chrysogenum* or *A. chrysogenum* which are deficient in the expression of nitrate reductase, which comprises a marker gene coding for nitrate reductase, operatively linked to a control sequence for expression of the said gene and wherein said marker gene coding for nitrate reductase is isolated from cells of the same species as the intended transformation host.

2. Vector DNA as claimed in claim 1 further comprising an industrially important gene linked in matching reading frame to said marker gene.

3. Vector DNA as claimed in claim 2 wherein said industrially important gene is selected from the group consisting of genes involved in antibiotic biosynthesis, genes which result in improved growth of the cells, genes which enable growth of the cells on a novel substrate and genes which will change the metabolite produced.

4. Vector DNA as claimed in claim 1 being Plasmid pSTA 1 (NCIMB 40102) or Plasmid pSTA 700 (NICMB 40103).

5. A transformed strain of *P. chrysogenum* or *A. chrysogenum* containing vector DNA as claimed in claim 1.

6. *Penicillium chrysogenum* strain S1900 (CMICC 330177) or *Acremonium chrysogenum* strain M1160 (CMICC 330178).

* * * * *